United States Patent [19]

Ferruti et al.

[11] 4,211,865

[45] Jul. 8, 1980

[54] NOVEL PROSTAGLANDIN PRECURSORS IN POLYMERIC FORM

[76] Inventors: Paolo Ferruti, V.le Cassiodoro, 24; Rodolfo Paoletti, V.le Regina Margherita, 43, both of Milan, Italy

[21] Appl. No.: 823,500

[22] Filed: Aug. 10, 1977

[30] Foreign Application Priority Data

Aug. 10, 1976 [IT] Italy ................ 26172 A/76

[51] Int. Cl.² ............................................. C08B 31/02
[52] U.S. Cl. ........................................ 536/48; 536/49; 536/51; 536/107; 536/108; 536/110; 536/112
[58] Field of Search .................. 536/49, 48, 51, 107, 536/108, 110, 112

[56] References Cited

U.S. PATENT DOCUMENTS

| Re. 28,809 | 5/1976 | Tessler | 536/110 |
|---|---|---|---|
| 2,954,372 | 9/1960 | Novak | 536/112 |
| 3,720,663 | 3/1973 | Tessler | 536/110 |
| 4,069,387 | 1/1978 | Hayashi et al. | 536/112 |

OTHER PUBLICATIONS

Condensed Chemical Dictionary, p. 349, 1956.
Whistler et al., Starch: Chemistry and Technology, 1965, pp. 358 and 376.

*Primary Examiner*—Melvyn I. Marquis
*Attorney, Agent, or Firm*—Joseph W. Molasky & Associates

[57] ABSTRACT

A novel polymer consisting of a macromolecular polysaccharide matrix which is esterified in whole or in part by activated polyunsaturated acids containing twenty carbon atoms. Typical of these acids are, for example, 8, 11, 14-eicosatrienoic acid, 5, 8, 11, 14-eicosatetraenoic acid and 5, 8, 11, 14, 17-eicosapentenoic acid. These polymers are therapeutically useful products which have utility in the same fields of application as the prostaglandins but absent their adverse side effects.

13 Claims, No Drawings

NOVEL PROSTAGLANDIN PRECURSORS IN POLYMERIC FORM

This invention relates to polymers which contain polyunsaturated aliphatic acid radicals bonded to macromolecular matrices of the polysaccharide type, to a method for their preparation and to pharmaceutical compositions comprising same.

More particularly, this invention relates to new polymers which have utility in human and animal therapy in the preparation of cosmetics and foodstuffs and in agricultural applications. However, the most important application is in human therapy and particular reference is made to this use hereinafter.

The novel polymers of this invention consist essentially of a macromolecular matrix of the polysaccharide type to which are bonded polyunsaturated aliphatic acid radicals which are precursors of prostaglandins in the organism.

The acids, the radicals of which are contained in the novel polymers of this invention, are acids containing 20 carbon atoms, and essentially 8,11,14-eicosatrienoic acid (di-homo-$\gamma$-linoleic acid), 5,8,11,14-eicosatetraenoic acid (arachidonic acid), and 5,8,11,14,17-eicosapentenoic acid, which respectively give rise to the following prostaglandins in the organism: $PGF_1 + PGE_1$; $PGF_{2\alpha} + PGE_2$; $PGF_{3\alpha} + PGE_3$.

In reality, only di-homo-$\gamma$-linoleic acid and arachidonic acid are present in the organism in measurable quantities and give rise to important quantities of prostaglandins. Eicosapentenoic acid is extremely unstable and both it and the relative prostaglandins are present in minimum quantities in the organism.

In the new polymers of this invention, the polyunsaturated acid radicals are bonded to the polysaccharide matrix by ester bonds which are totally but gradually hydrolysed in a host organism over a period of time which may be predetermined by suitable choice of the polysaccharide and the precentage of fatty acids bonded to it. Prostaglandins notably constitute one of the most intersting discoveries of recent years.

Chemically, these are unsaturated hydroxy acids with a skeleton of 20 carbon atoms partially cyclised to form a ring of 5 carbon atoms.

BACKGROUND

Prostaglandins have been classified into two large series which differ from each other in having in one case (PGF) two hydroxyl groups in the 5 atom carbon ring, and in the other case (PGE) a ketone group and a hydroxyl group in the same ring. There are also subclasses characterized by the presence of a double bond in a determined position or by the presence of several double bonds.

As stated, prostaglandins are formed in the organism by biosynthesis from polyunsaturated fatty acids containing 20 carbon atoms, and essentially 8,11,14-eicosatrienoic acid, 5,8,11,14-eicosatetraenoic acid, and 5,8,11,14,17-eicosapentenoic acid, which are liberated by an enzymatic process from the lipids present in an organism. Recent studies on prostaglandins have shown that these substances are responsible in the organism for a large number of biological mechanisms extending from fertility control to stimulating smooth musculature contractions, and influencing arterial tension, platelet aggregation, muscular and articular pains etc.

In practice, the large amount of work carried out has shown that the prostaglandins are of considerable use in solving the problem of birth control, by administration in doses sufficient to induce abortion.

However, the high hopes raised in this field have largely disappeared, and work on the practical use of prostaglandins has come to a sudden halt following the established appearance of side effects which it has not been possible to eliminate or control.

In this respect, it has been found that in order to obtain the desired fertility control or to induce abortion it is necessary to administer prostaglandins in such large doses that the other biological processes initiated by prostaglandins come into being, with the risk of inducing arterial hypertension, intestinal muscular contraction with vomit and diarrhoea, hemicrania, reduction in the pain threshold in muscles and joints, hyperthermia and platelet aggregation.

In a previous patent application (Italian application No. 28419 A/74) by the same inventors, high vinyl polymers containing radicals of prostaglandins or of their precursor fatty acids have been described.

These polymers, which may be used in human therapy in all fields in which prostaglandins are used, have the great advantage relative thereto of permitting controlled continuous feeding of prostaglandins, so avoiding the administration of large doses and the consequent heavy side effects. However, in continued experiments, certain important facts have emerged.

(1) The administration of polymers containing precursor fatty acids is preferable to the administration of polymers containing prostaglandin radicals in that the organism is able to utilize the specific biosynthetic enzymes of the prostaglandins and respect the differences between organs and tissues in the production of the specific endogenous prostaglandins required by the organism.

In contrast, the indiscriminate administration of a single specific synthesis prostaglandin can create unbalance in determined organs and/or tissues.

(2) The use of polymers containing prostaglandin precursor acid radicals is preferable to the use of polymers containing the prostaglandin radicals themselves in that where there is an unexpected or toxic reaction in the individual or animal, this may be immediately blocked by administering specific prostaglandin synthesis inhibitors such as acetylsalicylic acid, indomethacin and the like. This is evidently not possible when administering polymers directly containing the synthesic prostaglandins.

(3) While the use of macromolecular polyvinyl matrix polymers is satisfactory in oral or intra-uterine administration, in the case of parenteral administration it has been found that the vinyl polymer residue after separation of the prostaglandin or acid radicals is not degraded and thus eliminated from the organism, but tends to accumulate. This means that parenteral administration, which is highly desirable or even necessary in many cases, cannot be attained with these polymers, which constitutes a serious limitation to the use of the drugs.

(4) In an attempt to solve the aforesaid problems, the direct administration of the polyunsaturated aliphatic acid precursors of prostaglandins in the pure state has been considered. However, it has been found that acids thus administered become metabolised by the organism in a few minutes, to form only traces of prostaglandins.

THE INVENTION

The products of this invention are non-toxic polymers having a molecular weight of between 5,000 and 1,500,000 and consist essentially of a macromolecular polysaccharide matrix esterified in whole or in part with polyunsaturated aliphatic acids which are prostaglandin precursors.

The novel polymers of this invention exhibit surprisingly excellent results, in all respects, without any of the drawbacks encountered with the prostaglandins or pure acids, or with the vinyl polymers containing same.

In this connection, it has been found that in these polymers, which contain polyunsaturated prostaglandin precursor fatty acid radicals bonded by ester bonds to polysaccharide matrices, these bonds become totally but gradually hydrolysed in a biological environment to liberate the polyunsaturated acid radicals which are immediately transformed quantitatively in the organism into prostaglandins. Once the acid radicals have been hydrolysed, the polysaccharide matrices are degraded by the organsim into sugars, i.e., substances which exist in the organism and which, therefore, are certainly compatible therewith and easily eliminated.

The new polymers are essentially prepared by treating a totally or partially preformed polysaccharide, preferably chosen from the group consisting of soluble starches and dextrans, with a suitably activated polyunsaturated acid. An esterification reaction occurs and when this reaction is completed, the polymerisation of the polysaccharide may be completed.

Thus, the present polymers may be prepared in accordance with one of the following alternative methods:

Method I: A totally or partially polymerised polysaccharide which is available commercially and which possesses the required molecular weight is treated with an active derivative of a polyunsaturated fatty acid, preferably, an imidazolide, benzotriazolide, N-hydroxysuccinimide ester, N-hydroxyphthalimide ester, or N-hydroxybenzotriazole ester:

Imidazolide: 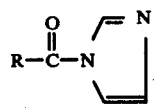

Benzotriazolide: 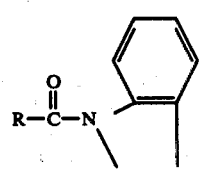

N-Hydroxysuccinimide ester: 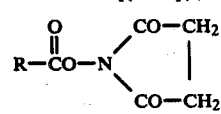

N-Hydroxyphthalimide ester: 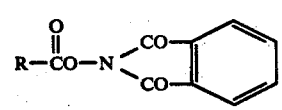

N-Hydroxybenzotriazole ester: 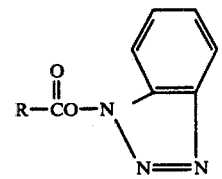

wherein R is a polyunsaturated fatty acid radical as herein defined.

These active derivatives are prepared by generally known methods for carboxylic acids (Angewandte Chemie-International Edition—vol. 1 (1962) page 351 et seq.) as, for example, by treating the chloride of the said acid with imidazole, benzotriazole, N-hydroxysuccinimide, N-hydroxyphthalimide or N-hydroxybenzotriazole, respectively, in an inert organic solvent, preferably, in the presence of an organic base such as pyridine or triethylamine.

In some cases it is also possible to use the chlorides of the acids or their anhydrides but, usually, the reaction takes place in a more controllable manner if one of the above derivatives is used so as to allow for a wider choice of reaction solvents. The preformed polysaccharides are carefully dried under high vacuum at temperatures of 10°–100° C. and they are then soaked or dissolved in inert organic solvents such as dimethylsulphoxide, N,N-dimethylformamide, N,N-dimethylacetamide, nitrobenzene etc., and are finally treated with the active derivatives of the acids at temperatures of 10°–90° C. for times varying from 15 minutes to some days, according to the polysaccharide used, the type of acid derivative, and the percentage of acid radicals to be introduced. In some cases the esterification reaction may be accelerated by using organic bases (e.g. triethylamine) as catalysts. In all cases the esterification reaction is 100% complete, because of which by fixing the initial ratio of polysaccharide to the activated acid derivative, it is possible to fix the percentage of acid radicals present in the final polymer and hence the quantity of acid liberated in the biological environment.

The polymers are precipitated by pouring the reaction product into a suitable non-solvent, preferably, ether if the degree of acylation is not very high, or water, lower alcohols or water-alcohol mixtures for higher degrees of acylation.

The polymers are purified by dissolving in a solvent and reprecipitating with a non-solvent. The type of solvent/non-solvent pair varies according to the type of polymer.

Finally the products are dried under vacuum, preferably, at ambient temperature.

Method II: A stoichiometric quantity or slight excess of N,N-carbonyldiimidazole is added to a solution of the desired acid and the new solution containing the acid imidazolide is mixed with a solution or suspension of the polysaccharide.

The reaction between the activated acid and polysaccharide again takes place at a temperature of 10°–90° C. for a time which varies from 15 minutes to some days.

The esterification reaction is again 100% complete and the separation and purification are performed as in Method I.

Method III: The desired polyunsaturated fatty acid and a carbodiimide (e.g. N,N-dicyclohexylcarbodiimide) are added to a solution or suspension of polysaccharide and the mixture is kept under agitation at a temperature of $-10°-50°$ C. for a time of one hour to 48 hours according to the polysaccharide and percentage of acid radicals to be introduced. The esterification reaction is again 100% complete. At the end of the reaction the ureas which have formed are filtered and the new polymer is precipitated and purified exactly as described for the previously illustrated process alternatives by means of a suitable non-solvent/solvent pair.

The novel polymers of this invention may be soluble in water, or insoluble but with the facility to swell in water, or insoluble in water but soluble in vegetable oils, according to the type of polysaccharide matrix chosen and the percentage of acid radicals contained therein. As the physical characteristics are previously determinable, it is possible to prepare polymers containing the desired prostaglandin precursor acid in the most suitable form for any type of administration, for example oral, parenteral or intra-vaginal.

The speed with which the ester bonds are hydrolysed and thus the quantity of prostaglandins formed in the organism in unit time and over a certain time period is previously determinable on the basis of the invention, i.e., other conditions being equal, the higher the degree of substitution the greater the quantity of free acid obtainable in the organism but the lower the speed of hydrolysis.

Obviously the speed of hydrolysis is a characteristic of each type of polymer (type of polysaccharide matrix and esterifying acid) and is also determinable in advance.

As it has been found that acids administered in the form of polymer are quantitatively converted into prostaglandins in the organism and as the useful prostaglandin doses and their limits of intolerance are well known, the dosing of the new polymers will be adjusted such as to give the useful prostaglandin quantity at a constant level over the required time, and always below the level which would induce undesirable side effects.

A whole series of tests was carried out with marked acids to show the difference in behaviour between free polyunsaturated aliphatic prostaglandin precursor acids and the new polymers according to the invention containing radicals of the same acids bonded to polysaccharide matrices when administered to a living organism.

Hereinafter, for simplicity, only the results of tests carried out with di-homo-$\gamma$-linoleic acid and with the polymer prepared in Example 1 below are given, this latter polymer consisting of a commercial B.D.H. dextran matrix of molecular weight between 200,000 and 250,000, the hydroxyl groups of which are esterified with radicals of di-homo-$\gamma$-linoleic acid to the extent of 22.5% of the total weight. The progress of hydrolysis and the distribution of the acid were the same for all polymers prepared in the following examples except that, as stated, it was found that the greater the percentage of acid contained in the polymer the lower the speed of hydrolysis, however the hydrolysis was total and the conversion into prostaglandins was quantitative.

With polymers of a higher percentage of esterification, there is thus a milder action more prolonged in time.

Di-homo-$\gamma$-linoleic acid marked with tritium (DH$\gamma$L-H$^3$) has been used both as free acid and for the preparation of the polymer of Example 1. Two solutions suitable for intravenous administration were prepared from these products.

Male cats having a weight of $4\pm0.2$ kg were used. The acid was administered to five cats intravenously in a single injection and the polymer was administered to a further five cats in a quantity containing the same amount of acid.

A measurement was made on the plasma of the total and specific activity of the DH$\gamma$L-H$^3$ present in the major lipid fractions (phospholipids, triglycerides, unesterified fatty acids) and the total activity (including the acid fraction still bonded to the polymer) at successive times. In both cases (free acid A-polymer B) the total radioactivity of the injected sample was 10 microcuries per cat.

The radioactivity of the plasma was determined after purifying the lipids by bidimensional thin layer chromatography, by removing the corresponding stains, eluting them and analysing the individual fatty acids by radiogaschromatography (a method which enables the fatty acid composition and specific radioactivity of each individual fatty acid to be determined simultaneously).

The results of this experiment are summarised in the following tables:

(1) Total radioactivity in CPM/mg acid

| time | 0 | 5 | 15 | 30 | 60 | 120 | 180 |
|---|---|---|---|---|---|---|---|
| A | $3.5 \cdot 10^5$ | $2 \cdot 10^4$ | $2 \cdot 10^2$ | n.v. | n.v. | n.v. | n.v. |
| B | $3.8 \cdot 10^5$ | $3 \cdot 10^5$ | $2 \cdot ^4$ | $1 \cdot 10^4$ | $5 \cdot 10^3$ | $2 \cdot 10^3$ | $2 \cdot 10^2$ |

(2) Radioactivity in phospholipids in CPM/mg acid

| time | 0 | 5 | 15 | 30 | 60 | 120 | 180 |
|---|---|---|---|---|---|---|---|
| A | $5 \cdot 10^4$ | $1 \cdot 10^3$ | $1 \cdot 10^2$ | n.v. | n.v. | n.v. | n.v. |
| B | $5 \cdot 10^4$ | $2 \cdot 10^4$ | $5 \cdot 10^3$ | $1 \cdot 10^3$ | $5 \cdot 10^2$ | $3 \cdot 10^2$ | $2 \cdot 10^2$ |

(3) Radioactivity in free fatty acids in CPM/mg acid

| time | 0 | 5 | 15 | 30 | 60 | 120 | 180 |
|---|---|---|---|---|---|---|---|
| A | $5 \cdot 10^3$ | $5 \cdot 10^2$ | $1 \cdot 10^2$ | n.v. | n.v. | n.v. | n.v. |
| B | $2 \cdot 10^3$ | $1 \cdot 10^3$ | $5 \cdot 10^2$ | $3 \cdot 10^2$ | $2 \cdot 10^2$ | $1 \cdot 10^2$ | $1 \cdot 10^2$ | n.v. = unable to be evaluated.

The above data shows that di-homo-$\gamma$-linoleic acid administered as such disappears very rapidly from the plasma and therefore cannot be utilised by the organism for the synthesis of prostaglandins. In contrast, when di-homo-$\gamma$-linoleic acid is administered in the form of a polysaccharide polymer, it is still present in the plasma in measurable quantities after three hours from administration. As it has been shown that the biosynthesis of endogenous prostaglandins depends on the available quantity of polyunsaturated precursor acid, it is evident that by administering di-homo-$\gamma$-lineoleic acid in the form of a polymer, it may be utilised for long periods of time for the biosynthesis of prostaglandins in the human or animal organism. From an anatomical-pathological and biochemical examination (hepatic, renal, cardiovascular and nervous parameters) on the animals treated with polymer B, it is found that any measurable toxic effects are completely absent.

A similar conclusion was reached after analysis of the animals treated with all other polymers of the composition illustrated in the following examples of preparation.

Pharmacological data is given hereinafter which shows the advantages obtainable with the new polymers according to the invention, containing prostaglandin precursor acid radicals, with respect to the use of the same prostaglandins in the free state.

From the aforegoing, the comparison cannot be made with the corresponding free precursor acids as these disappear in a few minutes from the plasma and form only prostaglandin traces. The experiments were carried out using anaesthetised cats having a weight of about 2 kg. Anaesthesia was induced with ethyl ether and maintained with a solution of chloralose and urethane (80:100) administered through the femoral vein.

A cannula was inserted in the trachea and femoral artery to record the pressure. A flask was inserted into the stomach to directly record the motility of the smooth musculature.

The polymer used in the particular test described (which for simplicity is indicated by C) is the polymer of Example 5 consisting of a B.D.H. dextran matrix of molecular weight between 200,000 and 250,000 esterified with arachidonic acid. However, analogous results were obtained with the other prepared polymers. The given doses of polymer refer to the quantity of prostaglandin corresponding to the precursor acid contained in the polymer. Consequently the measured values are directly comparable.

| Compound | Dose mg/kg | Mean reduction of arterial pressure Percent (%) in mm Hg | Activation of the stomach motility duration; in Minutes | Bronchospasma duration; in Seconds |
|---|---|---|---|---|
| PGF$_2$ | 1.0 | 63 | 42 | 36.17 |
| Polymer C | 0.350 | 60 | 120 | 16.5 |
| Polymer C | 0.700 | 55 | 180 | 16.7 |
| Dextran B.D.H. | 3.0 | 0 | 0 | 0 |

*Reduction of air flux

In the foregoing Table, the reduction in arterial pressure is an index of the "intensity" of the action, while the duration of activation of the stomach motility is an index of the "duration" of the prostaglandin action.

The bronchoplasma duration is an index of undesirable side effects.

From the data given in the table, the following is immediately deduced:

(a) The polymer containing arachidonic acid produces an effect which is approximately three times more intense than the corresponding preformed free prostaglandin.

(b) For equal activity, the polymer produces an effect which is three times longer than the corresponding free prostaglandin.

(c) The secondary effects with the polymer are considerably reduced and do not substantially increase even on doubling the dose.

From the pressure and motility data it can be deduced that the polymer is approximately nine times more active than the corresponding free prostaglandin in terms of prolongation of action, as an effect three times more prolonged was obtained with ⅓ of the dose.

More generally, it was found that the polymers according to the invention are five to fifty times more active then the corresponding free prostaglandins, where the activity is reckoned as the time duration of an effect of given intensity in relation to the dose. The purpose of the following examples is to illustrate some methods of preparation of the new polymers according to the invention without however having any limiting effect on the methods or the polymers prepared.

The following examples illustrate methods of carrying out the present invention, but it is to be understood that these examples are given for purposes of illustration and not by way of limitation.

EXAMPLE 1. Polymer; Dextran and Di-Homo-γ-Linoleic Acid Radicals.

Step A: Imidazolide of Di-Homo-γ-Linoleic Acid.

Di-homo-γ-linoleic acid (5.07 g.) was dissolved in pure anhydrous dichloromethane (50 ml) and after complete elimination of air using nitrogen or argon, imidazole (1.24 g.) was added under a stream of nitrogen. The mixture was mechanically agitated until a homogeneous solution was obtained; it was then cooled to 0°–5° C. in an ice bath and N,N-dicyclohexylcarbodiimide (3.77 g.) was added under a stream of nitrogen.

The reaction mixture was agitated at 0°–5° C. for 30 minutes, the ice bath was then removed and agitation was maintained for an additional four hours as the temperature rose to ambient temperature.

The reaction mixture was filtered over a glass filter into a weighed glass vessel from which the solvent was slowly evaporated under vacuum to afford 4.1 g. of clear viscous oil.

Anhydrous dimethyl sulphoxide was poured into the glass vessel under a stream of nitrogen to afford a solution containing the imidazolide of di-homo-γ-linoleic acid.

Step B: Polymer; Dextran and Di-Homo-γ-Linoleic Acid Radicals.

Commercial B.D.H. dextran of molecular weight 200,000 to 250,000 was carefully dried at 90° C. and 0.1 mm Hg for six hours. This product (3.75 g.) was then dissolved in anhydrous dimethylsulphoxide (37.5 ml) and placed in a vial. After eliminating the air in said vial with nitrogen, the imidazole of di-homo-γ-linoleic acid (1.08 g.) as prepared in Step A, supra, was added while maintaining the stream of nitrogen.

The reaction mixture was held at 40° C. for 72 hours by a controlled temperature bath and it was then poured into an excess of ether. The precipitated product was extracted twice with 200 ml of ether, filtered and dried at ambient temperature at 0.1 mm Hg.

There was thus obtained 4.20 g. of a dextran polymer containing 22.5% by weight of di-homo-γ-linoleic acid radicals.

By substituting benzotriazole for the imidazole of Example 1, Step A, and otherwise following the procedure described therein there is obtained the benzotriazolide of di-homo-γ-linoleic acid.

Also, upon substituting the said benzotriazolide of di-homo-γ-linoleic acid for the imidazolide of di-homo-γ-linoleic acid in Example 1, Step B, and otherwise following the procedure described therein there is thus obtained a dextran polymer containing di-homo-γ-linoleic acid radicals.

EXAMPLE 2. Polymer; Dextran and Di-Homo-γ-Linoleic Acid Radicals.

By following exactly the procedure described in Example 1 but varying the stoichiometric ratio of dextran to the imidazolide of di-homo-γ-linoleic acid, polymers were obtained having different degrees of acylation. The composition of said polymers and their solubility characteristics are given in Table I below.

TABLE I

| Dextran g | DMSO ml | Imidazolide g | % by weight of acyl groups in Product | Solubility in water* | Solubility in oil* |
| --- | --- | --- | --- | --- | --- |
| 3.75 | 40 | 1.5 | 30.5 | − | + |
| 3.75 | 40 | 1.08 | 22.5 | − | + |
| 3.75 | 40 | 0.8 | 17 | − | ⊕ |
| 3.75 | 40 | 0.6 | 12.5 | ⊕ | − |
| 3.75 | 40 | 0.4 | 8 | ⊕ | − |
| 3.75 | 40 | 0.3 | 6.5 | ⊕ | − |
| 3.75 | 40 | 0.2 | 3.8 | + | − |

*+ soluble
− insoluble
⊕ swollen
DMSO: Dimethylsulfoxide

EXAMPLE 3: Polymer; Starch and Di-Homo-γ-Linoleic Acid Radicals.

The procedure described in Example 1, Steps A and B, were repeated, but the polysaccharide employed in Step B was Merck soluble starch having an average molecular weight of 300,000. A series of polymers was obtained, the composition and solubility characteristics of which are shown in Table II by way of illustration.

TABLE II

| Soluble starch g | DMSO ml | Imidazolide g | % by weight of acyl groups in product | Solubility in water * | Solubility in oil * |
| --- | --- | --- | --- | --- | --- |
| 3.75 | 40 | 1.5 | 31 | − | + |
| 3.75 | 40 | 1.08 | 21.8 | − | ⊕ |
| 3.75 | 40 | 0.8 | 17.4 | − | ⊕ |
| 3.75 | 40 | 0.6 | 11.6 | ⊕ | − |
| 3.75 | 40 | 0.3 | 6 | + | − |
| 3.75 | 40 | 0.1 | 2.2 | + | − |

* + soluble
− insoluble
⊕ swollen
DMSO: Dimethylsulfoxide

Upon substituting N-hydroxysuccinimide, N-hydroxyphthalimide or N-hydroxybenzotriazole for the imidazole of Example 1, Step A, and otherwise following the procedure described therein, there are thus obtained the corresponding N-hydroxysuccinimide ester, N-hydroxyphthalimide ester and N-hydroxybenzotriazole of di-homo-γ-linoleic acid.

Upon substituting said N-hydroxysuccinimide ester, N-hydroxyphthalimide ester and N-hydroxybenzotriazole ester for the imidazole of di-homo-γ-linoleic acid in Example 1, Step B, and otherwise following the procedure described therein, there is thus obtained a polymer comprised of starch and di-homo-γ-linoleic acid radicals.

EXAMPLE 4. Polymer; Starch and Di-Homo-γ-Linoleic Acid Radicals.

Step A: Imidazolide of Di-Homo-γ-Linoleic Acid

Di-homo-γ-linoleic acid (5.61 g.) was dissolved in an anhydrous dimethylsulfoxide (22 ml.) in an inert gas atmosphere (nitrogen or argon) and N,N'-carbonyldiimidazole (3.4 g.) was added, again under an atmosphere of inert gas. Effervescence occurred, then additional dimethylsulfoxide (10 ml.) was added and the mixture was maintained at ambient temperature for three hours to afford the imidazolide of di-homo-γ-linoleic acid.

Step B: Polymer; Starch and Di-Homo-γ-Linoleic Acid Radicals.

Merck soluble starch (15.75 g.) having an average molecular weight of 300,000 was dissolved in hot anhydrous dimethylsulfoxide (160 ml.)

The mixture was cooled and the solution containing the imidazolide of di-homo-γ-linoleic acid as prepared in the previous stage was then added, again under an atmosphere of inert gas.

The reaction mixture was kept at 60° C. for three days and then poured into an excess of ether and extracted several times with fresh ether. It was dried at ambient temperature and 0.01 mm Hg. to afford 15.8 g. of a polymer containing 10.2% of di-homo-γ-linoleic acid radicals.

EXAMPLE 5. Polymers; Dextran and Arachidonic Acid Radicals.

Polymers were prepared as described under Example 2, but substituting the imidazolide of di-homo-γ-linoleic acid with the imidazolide of arachidonic acid.

A series of polymers was obtained with the same polysaccharide matrix and the same percentage of acid radicals as indicated in Table I, noting however that in this instance the acid radical percentages refer to arachidonic acid radicals.

It was found that the type of acid does not notably influence either the reaction conditions or the solubility characteristics of the polymers which, for these new polymers, are therefore as indicated in Table I for the corresponding polymers containing di-homo-γ-linoleic acid radicals.

EXAMPLE 6: Polymer; Starch and Arachidonic Acid Radicals.

Polymers were prepared as described in Example 3, but substituting imidazolide of arachidonic acid for the imidazolide of di-homo-γ-linoleic acid.

Polymers were obtained consisting of a starch matrix esterified with arachidonic acid.

Polymers with percentages of arachidonic acid corresponding to those indicated for the polymers of Table II were prepared essentially under the same conditions and were found to have the same solubility characteristics. Again, in this instance, it is apparent that the solubility characteristics depend essentially on the percentage of esterified groups present.

It should be understood that although this invention has been described with reference to particular embodiments, changes and modifications may be made within the intended scope of the following claims.

What is claimed is:

1. A non-toxic polymer having a molecular weight of between about 5,000 and 1,500,000 and consisting essentially of a macromolecular polysaccharide matrix selected from the group consisting of starch and dextran esterified with a polyunsaturated acid having 20 carbon atoms selected from the group consisting of 8,11,14- eicosatrienoic acid, 5,8,11,14-eicosatetraenoic acid and 5,8,11,14,17-eicosapentenoic acid.

2. A non-toxic polymer according to claim 1 in which the macromolecular polysaccharide matrix is dextran having a molecular weight of from about 200,000–250,000 and the polyunsaturated acid is 8,11,14-eicosatrienoic acid.

3. A non-toxic polymer according to claim 1 in which the macromolecular polysaccharide matrix is starch having an average molecular weight of 300,000 and the polyunsaturated acid is 8,11,14-eicosatrienoic acid.

4. A non-toxic polymer according to claim 1 in which the macromolecular polysaccharide matrix is dextran having a molecular weight of from about 200,000–250,000 and the polyunsaturated acid is 5,8,11,14-eicosatetraenoic acid.

5. A non-toxic polymer according to claim 1 in which the macromolecular polysaccharide matrix is starch having an average molecular weight of 300,000 and the polyunsaturated acid is 5,8,11,14-eicosatetraenoic acid.

6. A method for preparing a non-toxic polymer having a molecular weight of between about 5,000 and 1,500,000 and consisting essentially of a macromolecular polysaccharide matrix selected from soluble starch and dextran esterified with polyunsaturated acids having 20 carbon atoms and selected from the group consisting of 8,11,14-eicosatrienoic acid, 5,8,11,14-eicosatetraenoic acid and 5,8,11,14,17-eicosapentenoic acid; which comprises treating said 8,11,14-eicosatrienoic acid, 5,8,11,14-eicosatetraenoic acid or 5,8,11,14,17-eicosapentenoic acid or the acid halide or anhydride derivative thereof, with an heterocyclic amide or ester selected from the group consisting of imidazole, N,N'-carbonyldiimidazole, benzotriazole, N-hydroxysuccinimide, N-hydroxyphthalimide or N-hydroxybenzotriazole to afford the corresponding imidazolide, benzotriazolide, N-hydroxysuccinimide, N-hydroxyphthalimide or N-hydroxybenzotriazole intermediate, which intermediate is then treated with starch or dextran in an inert organic solvent to afford the desired polymer.

7. The method of claim 6 wherein the treatment of said acid, acid halide or acid anhydride with said imidazole, N,N'-carbonyldiimidazole, benzotriazole, N-hydroxysuccinimide, N-hydroxyphthalimide or N-hydroxybenzotriazole is conducted at temperatures in the range of from about 10°–90° C.

8. The method according to claim 6 wherein 8,11,14-eicosatrienoic acid is treated with imidazole to afford the corresponding imidazolide intermediate and said intermediate is treated with dextran in anhydrous dimethylsulphoxide to afford a dextran polymer of 8,11,14-eicosatrienoic acid.

9. The method according to claim 8 wherein dextran has a molecular weight of between about 200,000–250,000.

10. The method according to claim 6 wherein 8,11,14-eicosatrienoic acid is treated with imidazole to afford the corresponding imidazolide intermediate and said intermediate is treated with starch to afford a starch polymer of 8,11,14-eicosatrienoic acid.

11. The method according to claim 10 wherein the starch has an average molecular weight of about 300,000.

12. The method according to claim 6 wherein 5,8,11,14-eicosatetraenoic acid is treated with imidazole to afford the corresponding imidazolide intermediate and said intermediate is treated with dextran to afford the dextran polymer of 5,8,11,14-eicosatetraenoic acid.

13. The method according to claim 6 wherein 5,8,11,14-eicosatetraenoic acid is treated with imidazole to afford the corresponding imidazolide intermediate and said intermediate is treated with starch to afford the starch polymer of 5,8,11,14-eicosatetraenoic acid.

* * * * *